US010670573B2

(12) United States Patent
    Kidd, IV

(10) Patent No.: US 10,670,573 B2
(45) Date of Patent: Jun. 2, 2020

(54) CHLORIDE MEASUREMENT USING NON-HARSH REAGENTS

(71) Applicant: Hach Company, Loveland, CO (US)

(72) Inventor: Arnold Bertron Kidd, IV, Mishawaka (IN)

(73) Assignee: HACH COMPANY, Loveland, CO (US)

( * ) Notice: Subject to any disclaimer, the term of this patent is extended or adjusted under 35 U.S.C. 154(b) by 143 days.

(21) Appl. No.: 15/714,455

(22) Filed: Sep. 25, 2017

(65) Prior Publication Data

US 2019/0094198 A1    Mar. 28, 2019

(51) Int. Cl.
    *G01N 33/18*    (2006.01)
    *G01N 31/22*    (2006.01)
    *G01N 31/02*    (2006.01)

(52) U.S. Cl.
    CPC .......... *G01N 33/182* (2013.01); *G01N 31/02* (2013.01); *G01N 31/22* (2013.01)

(58) Field of Classification Search
    CPC ...... G01N 31/22; G01N 31/02; G01N 31/005; G01N 21/77; G01N 2021/7796; G01N 2021/6439; G01N 33/182
    See application file for complete search history.

(56) References Cited

U.S. PATENT DOCUMENTS 3,552,929 A * 1/1971 Fields et al. ........... A61B 5/441
                                                422/424
6,042,543 A    3/2000 Warwick et al.
2012/2889541   11/2012 Royer

FOREIGN PATENT DOCUMENTS

GB    2154737    9/1985
WO    89/02596   3/1989

OTHER PUBLICATIONS

Cate, David M. et al. "Simple, distance-based measurement for paper analytical devices." Lab on a Chip (2013) 13 2397. (Year: 2013).*
Phoonsawat, Kamonchanok et al. "A distance-based paper sensor for the determination of chloride ions using silver nanoparticles." Analyst (2018) 143 3867-3873. (Year: 2018).*
International Searching Authority, Notification of Transmittal of the International Search Report and the Written Opinion of the International Searching Authority, of the Declaration, dated Feb. 1, 2019, pp. 12.

* cited by examiner

*Primary Examiner* — Christopher Adam Hixson
(74) *Attorney, Agent, or Firm* — Ference & Associates LLC

(57) ABSTRACT

An embodiment provides a method for measuring ions in a solution, including: preparing a measurement device comprising an active indicator, wherein the active indicator comprises a silver complex; introducing the measurement device to a solution, wherein the silver complex reacts with the solution and generates a precipitation comprising one of the elements selected from the group consisting of: silver chloride, silver sulfide, and mixtures thereof; and measuring an amount of one of the elements selected from the group consisting of: chloride and sulfide, in the solution, wherein the measuring comprises identifying a peak of the precipitation on a portion of the measurement device and comparing the peak to a measurement chart.

20 Claims, 4 Drawing Sheets

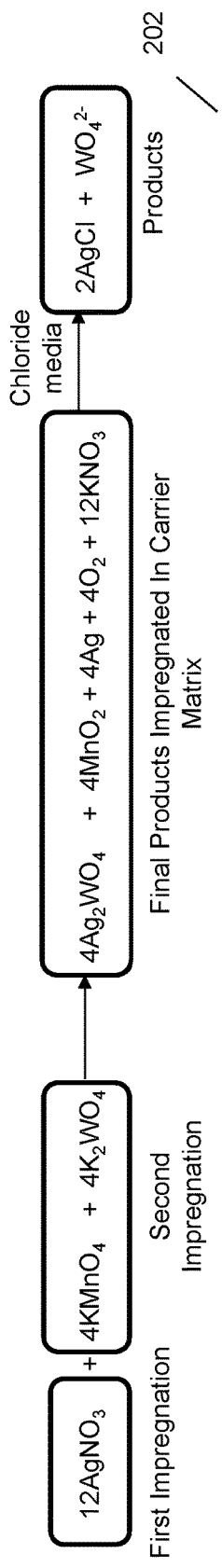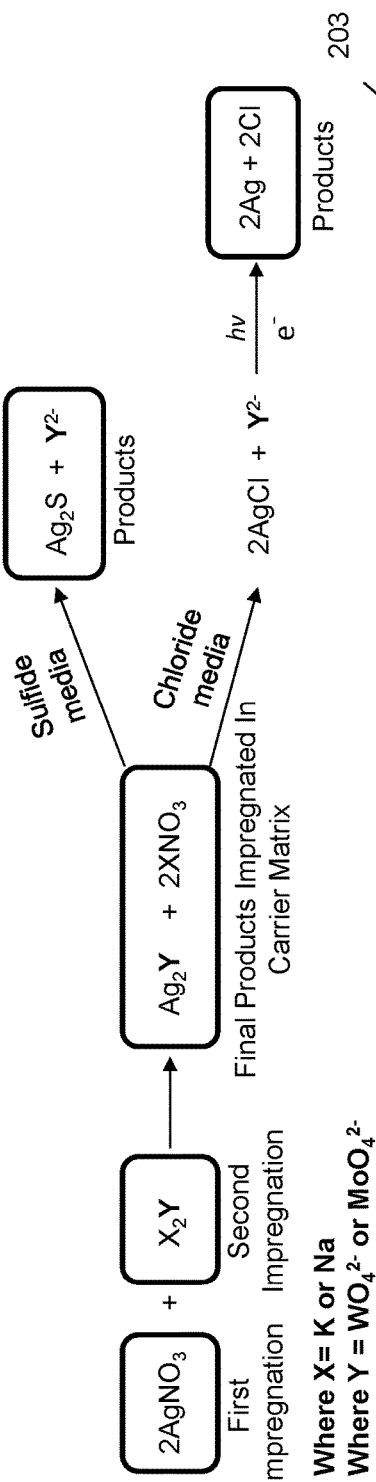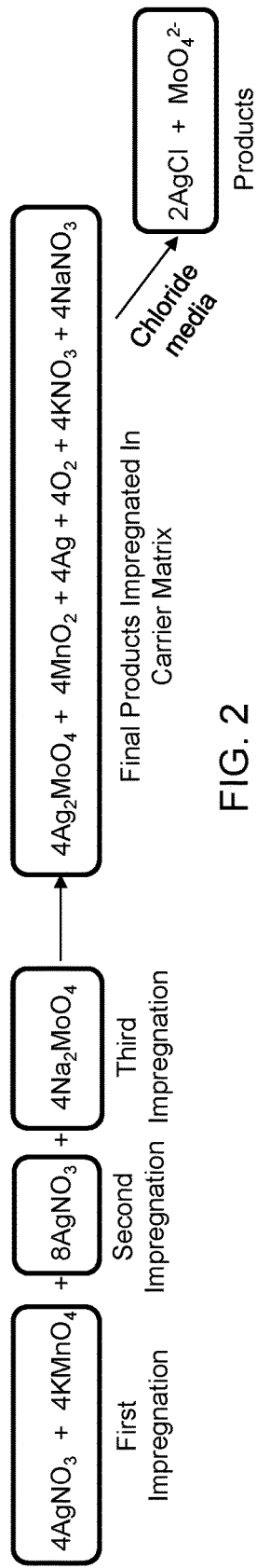
FIG. 2

STEP WISE REACTION FOR TUNGSTATE METHOD $$12AgNO_3 + 4KMnO_4 + 4K_2WO_4 \rightarrow 4Ag_2WO_4 + 4AgMnO_4 + 12KNO_3$$

First Impregnation — Second Impregnation $$4AgMnO_4 \xrightarrow{\Delta} 4MnO_2 + 2Ag_2O \xrightarrow{h\nu} 4Ag + O_2$$

CHLORIDE INDICATING REACTION $$Ag_2Y + 2Cl^- \rightarrow 2AgCl + Y^{2-}$$

Where $Y = WO_4^{2-}$ or $MoO_4^{2-}$

CHLORIDE INDICATING REACTION WITH WHITE BACKGROUND $$Ag_2Y + 2Cl^- \rightarrow 2AgCl + Y^{2-} \xrightarrow{e^-/h\nu} 2Ag + 2Cl$$

Where $Y = WO_4^{2-}$ or $MoO_4^{2-}$

$H_2S$ INDICATING REACTION WITH WHITE AND COLORED BACKGROUND $$Ag_2Y + S^{2-} \rightarrow Ag_2S + Y^{2-}$$

Where $Y = WO_4^{2-}$ or $MoO_4^{2-}$

FIG. 3

CHLORIDE MEASUREMENT USING NON-HARSH REAGENTS

BACKGROUND

This application relates generally to measuring chloride ions in aqueous or liquid samples, and, more particularly, to the measurement of chloride ions without the use of chromate or vanadium.

Ensuring water quality is critical in a number of industries such as pharmaceuticals and other manufacturing fields. Additionally, ensuring water quality is critical to the health and well-being of humans, animals, and plants which are reliant on the water for survival. One element that is typically measured is chloride. Too much chloride in water can be harmful to humans or animals, it can cause the water to have a bad taste or increased odor, and it can result in higher costs. Therefore, detecting the presence and concentration of chloride in water or other liquid solutions is vital.

BRIEF SUMMARY

In summary, one embodiment provides a method for measuring ions in a solution, comprising: preparing a measurement device comprising an active indicator, wherein the active indicator comprises a silver complex; introducing the measurement device to a solution, wherein the silver complex reacts with the solution and generates a precipitation comprising one of the elements selected from the group consisting of: silver chloride, silver sulfide, and mixtures thereof; and measuring an amount of one of the elements selected from the group consisting of: chloride and sulfide, in the solution, wherein the measuring comprises identifying a peak of the precipitation on a portion of the measurement device and comparing the peak to a measurement chart.

An embodiment provides a measurement device, comprising: an active indicator, wherein the active indicator comprises a silver complex; wherein the active indicator reacts with a solution introduced to the measurement device and generates a precipitation comprising one of the elements selected from the group consisting of: silver chloride, silver sulfide, and mixtures thereof; and a measurement chart, wherein the measurement chart identifies an amount of one of the elements selected from the group consisting of: chloride and sulfide, in the solution, by comparing a peak of the precipitation on a portion of the measurement device to the measurement chart.

An embodiment provides a method for measuring chloride ions in a solution, comprising: preparing a measurement device comprising a carrier matrix impregnated with an active indicator, wherein the active indicator comprises a silver tungstate complex; introducing the measurement device to a solution, wherein the silver tungstate complex reacts with the solution and generates a precipitation comprising silver chloride; and measuring an amount of chloride in the solution, wherein the measuring comprises identifying a peak of the precipitation on a portion of the measurement device and comparing the peak to a measurement chart operatively coupled to the measurement device.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

BRIEF DESCRIPTION OF THE SEVERAL VIEWS OF THE DRAWINGS

FIG. 2 illustrates an overall reaction for the tungstate method, an overall reaction for the tungstate and molybdate methods with a white background, and an overall reaction for the molybdate method with a colored background.

FIG. 3 illustrates a step wise reaction for the tungstate method.

DETAILED DESCRIPTION

Figure 1:
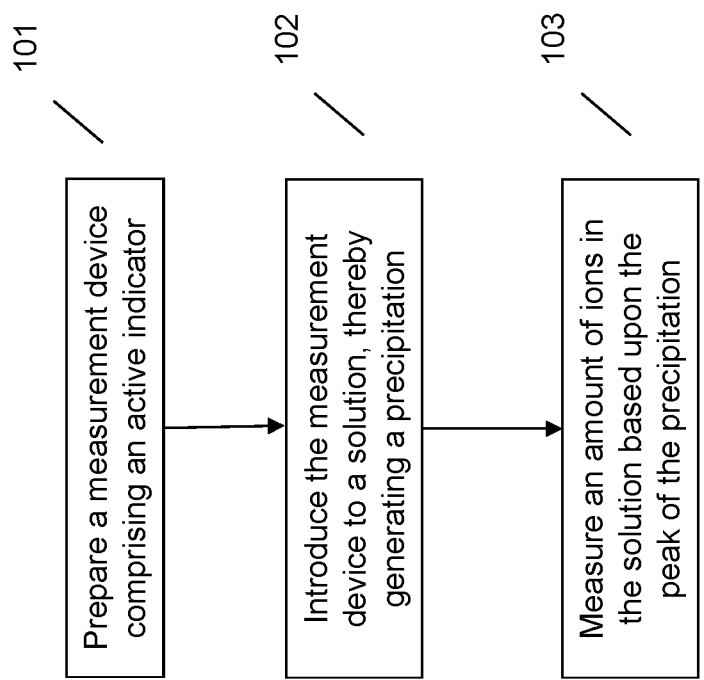
FIG. 1 illustrates an example method of measuring ions in a solution without using chromate or vanadium.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

The measurement of chloride in water or other solutions is very common. For example, chloride measurement may be used to determine the quality of water. High concentrations of chloride may be harmful to animals, humans, and/or plants. Accordingly, as another example, a user or entity may want the chloride in a body of water to be under a particular threshold, therefore, the user may measure the chloride in order to determine if the amount of chloride is under that threshold. Conventional techniques use chromium in its hexavalent form, for example, as silver chromate or silver dichromate, to measure chloride ions in water or other solutions. However, chromium in its hexavalent form is detrimental to the environment. Some countries are considering legislation to ban the use of chromium in its hexavalent form. Accordingly, one alternative is to use silver decavanadate instead of silver chromate or silver dichromate. However, potassium metavanadate, which is used to form the silver decavanadate, is an acute health hazard and is also detrimental to the environment. Additionally, because the supply of potassium metavanadate is low, the cost of this reagent is expensive and requires long lead times.

Accordingly, an embodiment provides a system and method for measuring ions, for example, chloride or sulfide ions, in a solution without using the harsh elements of chromate or vanadium. An embodiment may include a measurement device, for example, a carrier matrix including an impregnated active indicator, vial with solid active indicators, or the like. The active indicator may include a silver complex, for example, a silver tungstate complex, silver tungstate complex including silver oxide and manganese oxide derived from silver permanganate, a silver molybdate complex, or the like. Due to the fact that the cellulose of the carrier matrix may be white, the active indicator may be white, and the resultant reaction may produce a white precipitation, the active indicator may include silver oxide and manganese oxide derived from silver permanganate to generate a colored background on the carrier matrix or measurement device.

When the measurement device is introduced to a solution, the active indicator may react with ions in the solution and generate a precipitation. Depending on the makeup of the solution, the active indicator may react with the chloride in the solution to generate a precipitation comprising silver chloride, or may react with the sulfide in the solution to generate a precipitation comprising silver sulfide. Once the reaction has completed the amount of chloride or sulfide in the solution can be measured. Measuring the chloride or sulfide includes identifying the peak of the precipitation. The peak can then be compared with a calibrated measurement chart to determine the amount of chloride or sulfide in the solution.

The illustrated example embodiments will be best understood by reference to the figures. The following description is intended only by way of example, and simply illustrates certain example embodiments.

Referring now to FIG. 1, an embodiment may measure chloride in an aqueous or liquid solution. Additionally, using the techniques as described herein, an embodiment may be used to measure or detect sulfide in an aqueous or liquid solution. The techniques as described herein can be used to measure chloride or sulfide in a variety of different solutions, for example, water (e.g., drinking water, swimming pools, etc.), milk, sweat, blood, serum, concrete, urine, and the like, or may be used in a surface analysis for chloride contamination using other modified procedures.

In one embodiment, at 101, a measurement device may be prepared including an active indicator. In one embodiment the measurement device may include a carrier matrix. A carrier matrix may include a filter paper made of cellulose. Generally, the filter paper is of a white color. The active indicator may be impregnated on the filter paper within the carrier matrix. A carrier matrix measurement device may include the filter paper sandwiched between two pieces of polyester film, plastic sheets, or the like. This film or plastic may be printed on before or after incorporation into the carrier matrix. Alternatively, the measurement device may include a vial housing a solid form of the active indicator, for example, as a powder, capsule, pill, or the like.

In one embodiment the measurement device may include a printed measurement chart that is part of the measurement device, for example, the measurement chart may be printed on one or both pieces of the mylar or plastic encapsulating the filter paper in the carrier matrix embodiment. As another example, the measurement chart may be printed on a side of the vial. Alternatively, the measurement chart may be a part separate from the portion of the measurement device housing the active indicator. For example, the measurement chart may be included on a piece of paper, laminated paper, plastic, or the like, that is separate from the portion of the measurement device housing the active indicator.

The active indicator may include a silver complex. In one embodiment the silver complex may include a silver tungstate complex. Due to the fact that the filter paper is white, and the silver tungstate complex is white, potassium permanganate may be introduced to create a colored background. The potassium permanganate reacts with free silver in the matrix to form silver permanganate. Upon drying of the matrix, the silver permanganate will undergo reactions that produce manganese dioxide and silver oxide which color the paper. In an alternative embodiment the silver complex may include a silver molybdate complex. Alternatively, if the background is not colored, a dark colored peak can be generated by exposing the paper to light. Over time the exposure to light will cause the silver chloride to further react and form silver metal and chloride. The silver metal will take the same shape that the silver chloride had, thus, generating a colored peak on the white paper.

At 102 the measurement device is introduced to a solution. This solution may include any aqueous or liquid solution, for example, water, milk, blood, sweat, concrete, or the like. Using the carrier matrix, the carrier matrix may be dipped in the solution which causes the solution to wick up the filter paper. In the case of a vial, the solution may be introduced into the vial to mix with the active indicator. The solution then reacts with the active indicator to generate a precipitation. Additionally, as discussed above, the filter paper may be impregnated with silver permanganate to create the colored background for visualization of the white precipitation.

Depending on the makeup of the solution, the precipitation may either include silver chloride or silver sulfide. In other words, if the solution includes chloride ions, the precipitation may be silver chloride. On the other hand, if the solution includes sulfide ions, the precipitation may be silver sulfide. In the case of silver sulfide, the solution may require larger amounts of sulfide to cause a reaction than a correspond solution having chloride ions. In other words, the measurement device may be unable to detect trace or very small amounts of sulfide in the solution. However, the measurement device may be able to detect trace or small amounts of chloride in the solution.

Shown in FIG. 2 are three overall chemical reactions. 201 illustrates an overall reaction for the tungstate method including silver permanganate. The first impregnation on the carrier matrix is a clear solution of the silver nitrate. The second impregnation on the carrier matrix is a purple solution including the potassium permanganate and potassium tungstate. The reaction of the first and second impregnation result in the final products impregnated on the carrier matrix that include white, brown, and black complexes thereby creating a colored paper. When the impregnated colored paper is introduced to the chloride media, the resulting precipitate is white, which can be seen on the colored paper. FIG. 3 illustrates the step wise reaction for the tungstate. FIG. 3 also illustrates the reaction that occurs when the active indicator reacts with sulfide and the resulting indicating reaction on either a white or colored background.

Referring back to FIG. 2, 202 illustrates an overall reaction for the tungstate or molybdate methods with a white background. The first and second impregnation are clear solutions. Accordingly, the final products impregnated on the carrier matrix are white. When the carrier matrix is introduced to a sulfide media, the resulting products are black, which can be seen on a white background or paper not impregnated with silver permanganate. Alternatively, when the carrier matrix is introduced to the chloride media and exposed to light, the resulting products are also black. Again, this precipitation can be seen on a white background or paper.

Figure 4:
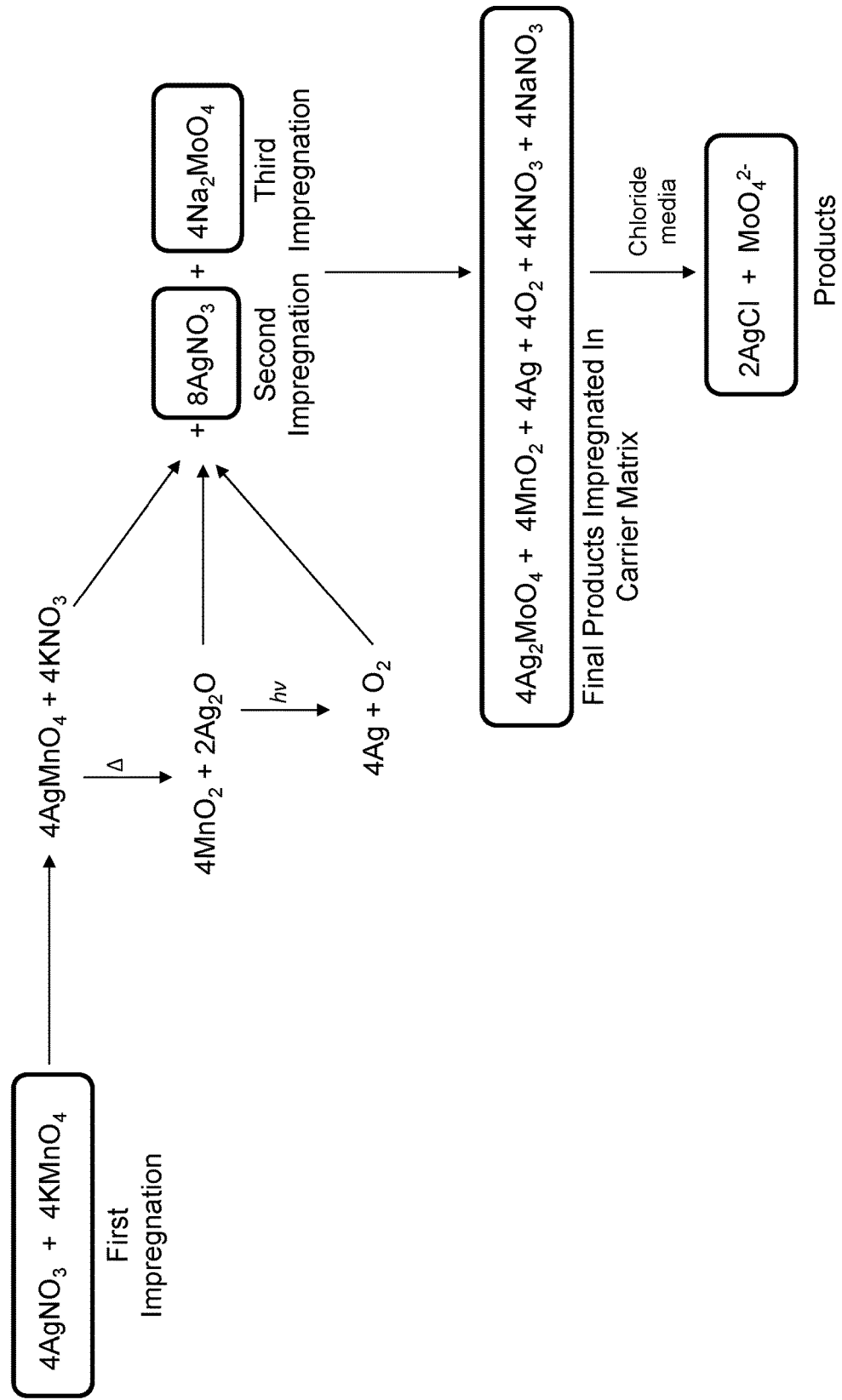
FIG. 4 illustrates a step wise reaction for the molybdate method with a colored background.

203 illustrates an overall reaction for molybdate with a colored background. The first impregnation is a purple solution, which may contain silver nitrate and potassium permanganate which are mixed to form silver permanganate. The second and third impregnations are clear solutions. Thus, the final products impregnated on the carrier matrix include white, brown, and black complexes, thereby coloring the paper. When the carrier matrix is then exposed to the chloride media, the resulting precipitate is white which can be seen on the colored paper. FIG. 4 illustrates a step wise reaction for molybdate with a colored background.

In the use cases of colored backgrounds, the color can also indicate how dry the carrier matrix paper is. For example, when the paper is wet, the color may be a bright purple, as the paper dries and once dried the paper turns a brown color. Accordingly, the color of the paper may be used to visualize the dryness of the paper. Additionally, the color of the paper may be lightened or darkened by adding alcohol to the mixture and/or by increasing or decreasing the drying temperature.

Once the reaction has completed the amount of chloride or sulfide contained within the solution can be identified or measured. Measuring the amount of chloride or sulfide includes identifying the peak of the precipitation, for example, the peak of the precipitation on the carrier matrix. Once the peak has been identified, the peak can be compared to the measurement chart to determine the amount of chloride or sulfide included in the solution. For example, the peak may reach a particular line or point on the calibrated measurement chart. This line or point may correspond to a particular volume or amount of chloride or sulfide included in the sample. The measurement chart may be calibrated based upon response of analyte of solution, for example, by using several devices and testing at various levels to generate a curve that indicates a particular marking corresponds to a parts-per-million (ppm) of chloride.

The measurement may either be done manually by a user or may be completed using an application or device assisted method. For example, in one embodiment an image of the carrier matrix may be taken with an information handling device. The image may then be compared against a measurement chart, for example, as included on the measurement device, stored in a data storage location accessible by the device, or the like. The device may then provide a reading or value of the amount of chloride or sulfide included in the solution.

The various embodiments described herein thus represent a technical improvement to conventional chloride measurement techniques. Using the techniques as described herein, an embodiment may use a silver tungstate complex for measuring the chloride in a liquid solution. Alternatively, one technique uses a silver molybdate complex for measuring the chloride in a liquid solution. Both techniques eliminate the need for harsh chromate or vanadium complexes for measuring chloride. Such techniques provide a more environmentally friendly and cost effective technique for measuring chloride in an aqueous or liquid solution.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a hand held measurement device, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for measuring ions in a solution, comprising:
preparing a measurement device comprising an active indicator, wherein the active indicator comprises a silver complex, wherein the measurement device comprises a carrier matrix comprising filter paper sandwiched between two pieces of film or plastic and wherein the active indicator is impregnated onto the filter paper;

introducing the measurement device to a solution, wherein the silver complex reacts with the solution and generates a precipitation comprising one of the elements selected from the group consisting of: silver chloride, silver sulfide, and mixtures thereof; and measuring an amount of one of the elements selected from the group consisting of: chloride and sulfide, in the solution, wherein the measuring comprises identifying a peak of the precipitation on a portion of the measurement device and comparing the peak to a measurement chart.

2. The method of claim 1, wherein the measuring an amount comprises measuring an amount of chloride.

3. The method of claim 1, wherein the silver complex comprises a silver tungstate complex.

4. The method of claim 3, wherein the silver tungstate complex further comprises silver oxide and manganese oxide.

5. The method of claim 4, wherein the measurement device comprises a carrier matrix comprising a colored background and wherein the precipitation produces a white precipitation peak.

6. The method of claim 1, wherein the silver complex comprises a silver molybdate complex.

7. The method of claim 1, wherein the precipitation comprises silver sulfide and wherein the measurement device comprises a carrier matrix comprising a white background and wherein the precipitation produces a dark precipitation peak.

8. The method of claim 1, wherein the measurement device comprises a vial and wherein the silver complex comprises at least one solid contained within the vial.

9. The method of claim 1, wherein the measuring an amount comprises measuring an amount of sulfide.

10. The method of claim 1, wherein the measurement chart is operatively coupled to the measurement device.

11. A measurement device, comprising:
filter paper sandwiched between two pieces of film or plastic;
an active indicator impregnated onto the filter paper, wherein the active indicator comprises a silver complex;
wherein the active indicator reacts with a solution introduced to the measurement device and generates a precipitation comprising one of the elements selected from the group consisting of: silver chloride, silver sulfide, and mixtures thereof; and
a measurement chart, wherein the measurement chart identifies an amount of one of the elements selected from the group consisting of: chloride and sulfide, in the solution, by comparing a peak of the precipitation on a portion of the measurement device to the measurement chart.

12. The measurement device of claim 11, wherein the measurement chart identifies an amount of chloride.

13. The measurement device of claim 11, wherein the silver complex comprises a silver tungstate complex.

14. The measurement device of claim 13, wherein the silver tungstate complex further comprises silver oxide and manganese oxide.

15. The measurement device of claim 11, wherein the precipitation comprises silver sulfide and wherein the measurement device comprises a carrier matrix comprising a colored background and wherein the precipitation produces a white precipitation peak.

16. The measurement device of claim 11, wherein the silver complex comprises a silver molybdate complex.

17. The measurement device of claim 16, wherein the measurement device comprises a carrier matrix comprising a white background and wherein the precipitation produces a dark precipitation peak.

18. The measurement device of claim 11, wherein the measurement device comprises a vial and wherein the silver complex comprises at least one solid contained within the vial.

19. The measurement device of claim 11, wherein the measurement chart identifies an amount of sulfide.

20. A method for measuring chloride ions in a solution, comprising:
preparing a measurement device comprising a carrier matrix impregnated with an active indicator, wherein the active indicator comprises a silver tungstate complex, the carrier matrix comprising filter paper sandwiched between two pieces of film or plastic;
introducing the measurement device to a solution, wherein the silver tungstate complex reacts with the solution and generates a precipitation comprising silver chloride; and
measuring an amount of chloride in the solution, wherein the measuring comprises identifying a peak of the precipitation on a portion of the measurement device and comparing the peak to a measurement chart operatively coupled to the measurement device.

* * * * *